(12) United States Patent
Samadpour

(10) Patent No.: US 8,911,990 B2
(45) Date of Patent: Dec. 16, 2014

(54) FOOD SAMPLE COLLECTOR

(75) Inventor: Mansour Samadpour, Seattle, WA (US)

(73) Assignee: Institute for Environmental Health, Inc., Lake Forest Park, WI (US)

(*) Notice: Subject to any disclaimer, the term of this patent is extended or adjusted under 35 U.S.C. 154(b) by 2038 days.

(21) Appl. No.: 11/718,766

(22) PCT Filed: Nov. 7, 2005

(86) PCT No.: PCT/US2005/040491
§ 371 (c)(1), (2), (4) Date: Jan. 4, 2008

(87) PCT Pub. No.: WO2006/057808
PCT Pub. Date: Jun. 1, 2006

(65) Prior Publication Data
US 2008/0102442 A1 May 1, 2008

Related U.S. Application Data

(60) Provisional application No. 60/625,302, filed on Nov. 5, 2004, provisional application No. 60/674,912, filed on Apr. 26, 2005.

(51) Int. Cl.
*C12M 1/26* (2006.01)
*G01N 1/08* (2006.01)

(52) U.S. Cl.
CPC ............................ *C12M 1/262* (2013.01)
USPC .................. 435/309.1; 73/864.41; 600/564; 606/167; 606/180

(58) Field of Classification Search
CPC ............ A61B 2017/320064; A61B 10/0266; A61B 10/0275; G01N 1/04; G01N 1/08
USPC ........ 435/309.1; 600/564, 567, 568; 606/171, 606/180; 73/864.41, 864.43; 175/20, 77
See application file for complete search history.

(56) References Cited

U.S. PATENT DOCUMENTS

| | | | |
|---|---|---|---|
| 2,896,444 A | 7/1959 | Forman et al. | |
| 4,252,200 A | 2/1981 | Peterson | |
| 4,383,583 A | 5/1983 | Baker | |
| 4,919,146 A | 4/1990 | Rhinehart | |
| 5,209,129 A | 5/1993 | Jaselskis et al. | |
| 5,423,824 A * | 6/1995 | Akerfeldt et al. | 606/80 |
| 5,722,985 A * | 3/1998 | Pettus | 606/180 |
| 6,676,677 B2 | 1/2004 | Klein | |

FOREIGN PATENT DOCUMENTS

JP 63062610 A * 3/1988
SU 1519656 A * 11/1989

* cited by examiner

Primary Examiner — William H Beisner
(74) Attorney, Agent, or Firm — Barry L. Davison; Davis Wright Tremaine LLP

(57) ABSTRACT

The present invention provides novel methods and devices for detection of pathogens or other microbes in an analyzed sample (e.g., food, industrial, pharmaceutical, botanical, environmental etc., sample). The inventive methods and devices provide for increasing the power of detection for pathogens on food surfaces, comprising increasing the number of independent, discrete samples taken during the sampling procedure. The inventive sampling device reduces sampling costs by minimizing time, material and product loss relative to prior art sampling techniques. In particular aspects, a novel surface sampling device for bulk solid foods is provided that operates to remove (e.g., shave) small pieces from contacted product (e.g., product pieces). The device comprises a sampling mechanism having utility to remove samples (e.g., cut slivers from) larger pieces of food or other sample materials. In particular embodiments, the device comprises a primary shaft member (e.g., cylindrical stainless steel), and a shaving means.

17 Claims, 15 Drawing Sheets

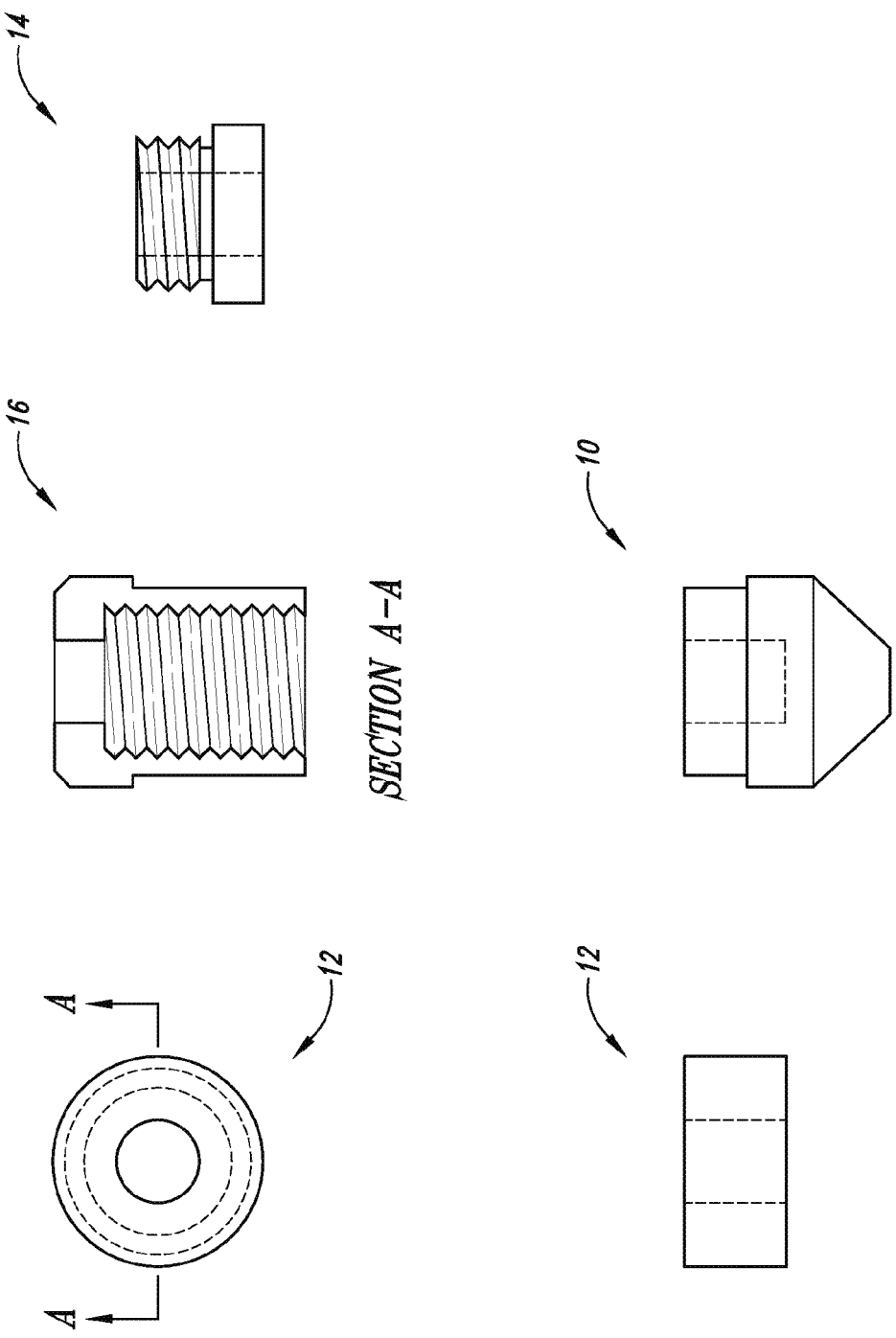

FOOD SAMPLE COLLECTOR

CROSS-REFERENCE TO RELATED APPLICATIONS

This application claims the benefit of priority to U.S. Provisional Patent Application Ser. No. 60/674,912, filed on 26 Apr. 2005 and entitled "FOOD SAMPLE COLLECTOR," and to Ser. No. 60/625,302, filed on 5 Nov. 2004 of same title, both of which are incorporated herein by reference in their entirety.

FIELD OF THE INVENTION

Aspects of the present invention relate generally to improving the efficiency of pathogen detection for increasing the safety and quality of food products, and more particularly to novel methods and devices for increasing the number of independent, discrete samples taken during a pathogen detection sampling procedure, thereby increasing pathogen detection power, and providing sampling cost savings by minimizing time, material and product loss.

BACKGROUND

One of the main objectives of the food industry is to continually improve the safety and quality of its products. To accomplish this objective, the industry must constantly monitor the efficacy of implemented food safety programs. One such exemplary monitoring program involves sampling of product to verify the absence of pathogens such as *Escherichia coli* O157:H7, *Salmonella* spp., and *Listeria monocytogenes*.

Current food sampling techniques, as performed by the industry, are primarily manual procedures that involve either cutting of food pieces, or swabbing surfaces using sponges. These procedures consume substantial time and material, are laborious, and promote product contamination via multiple handling steps.

Typical sampling plans for meat products follow a 'two-class' attribute plan, based on testing for the presence (positive result) or absence (negative result) of an organism. For example, following conventions set forth by the International Commission on Microbiological Specifications for Foods (ICMSF) (ICMSF; Microorganisms in Foods, Kluwer Academic/Plenum Publishers, 2002), for 'two-class' attribute plans, the probability of acceptance ($P_a$) for a lot is a function of three factors. The first is the actual incident rate (IR) of *E. coli* O157:H7 in a lot at a given sampling point. The second is "n", representing the number of sample units collected for the lot, and the third is "c", representing a maximum allowable number of sample units yielding unsatisfactory results for the lot.

The US Department of Agriculture Food Safety Inspection Service has a zero tolerance level for *E. coli* O157:H7 in non-intact beef products (see USDA-FSIS: United States Department of Agriculture Food Safety and Inspection Service; 1999 FSIS Policy on non-intact raw beef products contaminated with *E. coli* O157:H7; Food Safety and Inspection Service, U.S. Department of Agriculture, Washington, D.C. (available online; http://www.fsis.usda.gov/OA/background/O157policy.htm)). A significant consequence of the USDA-FSIS zero tolerance level for *E. coli* O157:H7 is that a lot of product is defective as soon as a positive result is obtained from a sample unit. No sampling plan can guarantee the complete absence of a pathogen unless all material in the lot is sampled, which is a practical impossibility. Furthermore, it is not yet commercially possible to produce product that is completely free of pathogens. Therefore, it is impossible to a priori design a sampling plan that will meet USDA-FSIS requirements. However, it would be highly desirable to improve the level of confidence of detecting pathogens in meat products if they are present.

Therefore, there is a pronounced need in the art for methods and apparatus to increase the power of detection for pathogens present in, e.g., meat products. There is a pronounced need in the art for methods and devices allowing for more sanitary sampling with reduced sample handling, and that allow for increased speed of sampling. There is a pronounced need in the art for methods and devices allowing for reduction of the cost of sampling materials, and for devices and equipment that may be easily sterilized prior to reuse. There is a pronounced need in the art for methods and devices enabling reduction of product loss by allowing for sampling smaller discrete pieces. There is a pronounced need in the art for methods and devices that allow for increasing the power of pathogen detection by taking a significantly higher number of representative samples in a cost-effective manner that reduces product waste, while precluding the necessity to sample all material.

SUMMARY OF THE INVENTION

The present invention provides novel methods and devices for detection of pathogens or other microbes in various analyzed samples (e.g., food, industrial, pharmaceutical, botanical, environmental, etc.).

In preferred aspects, a novel surface sampling device for bulk solid foods is provided. The inventive sampling device operates to remove (e.g., shave) small pieces from, for example, each product piece that it comes into contact with. The device comprises a sampling mechanism having utility to remove samples (e.g., cut slivers from), for example, larger pieces of food. In particular embodiments, the device is a two-part unit comprising primary shaft member (e.g., cylindrical stainless steel), and a housing comprising one or more shaving means. Alternately, the device may be unitary, or effectively unitary, comprising shaft and sampling elements.

The novel methods and devices provide for increasing the power of detection for pathogens on food surfaces by increasing the number of independent, discrete samples taken during the sampling procedure. The inventive sampling devices reduce sampling costs by minimizing time, material and product loss relative to prior art sampling techniques.

Particular aspect provide a surface sampling device for increasing the number of discrete surface samples taken during sampling of a multi-piece sample, comprising: a cylindrical housing having external and internal surfaces defining a housing wall, a sample-proximal end having an opening therein, a sample-distal end having an opening therein, and an internal channel between the ends, the channel generally defining an axis and a forward direction toward the sample-proximal end; at least one aperture within the housing wall, the aperture in communication with the internal channel and comprising a directional sample cutting or shaving surface at an external edge thereof, the directional cutting or shaving surface operative with the aperture upon rotation of the housing, to direct cuttings or shavings toward the internal channel; and a shaft member having a diameter less than the internal housing diameter and receivable into the housing at the sample-proximal housing end, the shaft member comprising: a sample-distal shaft end insertable through and extending beyond the sample-distal housing end opening; a sample-proximal shaft end-cap receivable into the sample-proximal housing end opening to seal the opening; a shaft attachment member positioned on the shaft between the distal shaft end and the shaft end-cap, the attachment member receivable into the sample-distal housing end and positioned at a distance from the shaft end-cap to hold the end-cap in sealable communication with the sample-proximal housing end opening; and a piston in communication with the internal housing surface and positioned on the shaft between the shaft attachment member and the shaft end-cap and defining a sample collecting chamber within the internal channel between the piston and the end-cap, and wherein the at least one aperture is in communication with the collecting chamber.

Preferably, the shaft attachment member is threaded and receivable into complementary thread receiving means in the sample-distal housing end to lock the housing onto the shaft. In particular embodiments, the threads are reverse threaded with respect to an operative rotational direction of the sampling device. In certain embodiments, the at least one aperture comprises an elongated opening running parallel to the housing channel axis. In particular aspects, the at least one aperture is framed with a turned-down or beveled leading edge, with respect to a direction of rotation, and a sharpened trailing edge to allow the device, during rotational operation thereof to perform a cutting or shaving action. Preferably, the device comprises a plurality of apertures, either positioned randomly along the wall of the sample collecting chamber or positioned in a symmetrical array along the wall of the sample collecting chamber. In certain aspects, the shaft diameter is less than one-half the outside diameter of the piston.

Additional aspects provide a method for enhanced sampling of multi-piece samples, comprising: obtaining a test sample comprising multiple pieces; rotating one of the sampling devices described herein by rotating the sample-distal shaft end extending beyond the sample-distal housing end opening; introducing the rotating sampling device into the test sample to obtain multiple sample surface cuttings or shavings from the multiple pieces or from a representative fraction thereof; and recovering the multiple sample surface cuttings or shavings from the device to provide for a collected sample comprising discrete surface samples. Preferably, 'introducing' comprises at least one repetition of forward introduction of the device into the test sample and retrieval of the device in the reverse direction from the test sample. Preferably, there is a plurality of repetitions through different sampling paths within the test sample. In particular aspects, recovering the multiple sample surface cuttings or shavings from the device comprises unlocking the shaft from the housing, removing the shaft from the housing to expose the piston, and recovering the surface cuttings or shavings from the sample collecting chamber and the at least one aperture.

Yet further aspects provide a surface sampling device for increasing the number of discrete surface samples taken during sampling of a multi-piece sample, comprising: a cylindrical member having and external surface, a sample-proximal end, a sample-distal end, the cylindrical member generally defining an axis and a forward direction toward the sample-proximal end; at least one channel extending into the cylindrical member from the external surface thereof, the channel comprising a sample collection chamber and a directional sample cutting or shaving surface at an external edge thereof, the directional cutting or shaving surface operative with the channel, upon rotation of the cylindrical member, to direct cuttings or shavings into the channel and collection chamber; and a cylindrical shaft integral with, or lockingly receivable into the cylindrical member at the sample distal end thereof, the cylindrical shaft suitable to operatively rotate the cylindrical member when rotational force is applied to the cylindrical shaft. In particular embodiments, the at least one channel comprises an elongated opening running parallel to the axis of the cylindrical member. Preferably, the at least one channel is framed with a turned-down or beveled leading edge, with respect to a direction of rotation, and a sharpened trailing edge to allow the device, during rotational operation thereof to perform a cutting or shaving action. In particular aspects, there is a plurality of channels positioned either randomly along the external surface of the cylindrical member, or positioned in a symmetrical array along the external surface of the cylindrical member.

SUMMARY OF THE DRAWINGS

FIGS. 1A, 1B, 1C and 3 show an exemplary sampling device 2 comprising a two-part unit having a primary shaft member (e.g., cylindrical stainless steel) 4, and a housing 6 comprising one or more shaving means 8.

FIG. 3, shows, according to a preferred embodiment, representative dimensions for several of the device elements of FIG. 1A.

FIG. 5 shows the embodiment of FIG. 4A attached to an electric drill. FIG. 6 shows the exemplary embodiment of FIG. 1C used to collect a sample of food. FIG. 7 shows a similar sample collected using the embodiment of FIG. 4A, and shows that the sampled (e.g., shaved and grated) food product is contained in the well of the fluted opening. FIG. 8 shows how the sample collected from the embodiment of FIG. 1C can be removed for subsequent laboratory analysis.

FIGS. 10A, 10B and 10C show portions of beef (approximating the size and nature of those found in 'combos' during the production of beef products) spray painted to distinctively mark their surfaces. FIG. 11 shows the embodiment of FIG. 4B after it was withdrawn from the container containing the discrete colored layers. Many colors are represented in the collected sample contained in the well of the fluted opening. FIG. 12 shows the collected sample after removal from the well of the fluted opening, and confirms that the embodiment removed discrete portions of material from all of the discrete colored layers present in the container.

FIG. 14A shows an exemplary four-flute design with non-beveled cutting edges. FIG. 14B shows an exemplary four-flute design with beveled cutting edges. FIG. 14C shows an exemplary three-flute design with non-beveled cutting edges.

DETAILED DESCRIPTION OF THE INVENTION

Figure 1A:
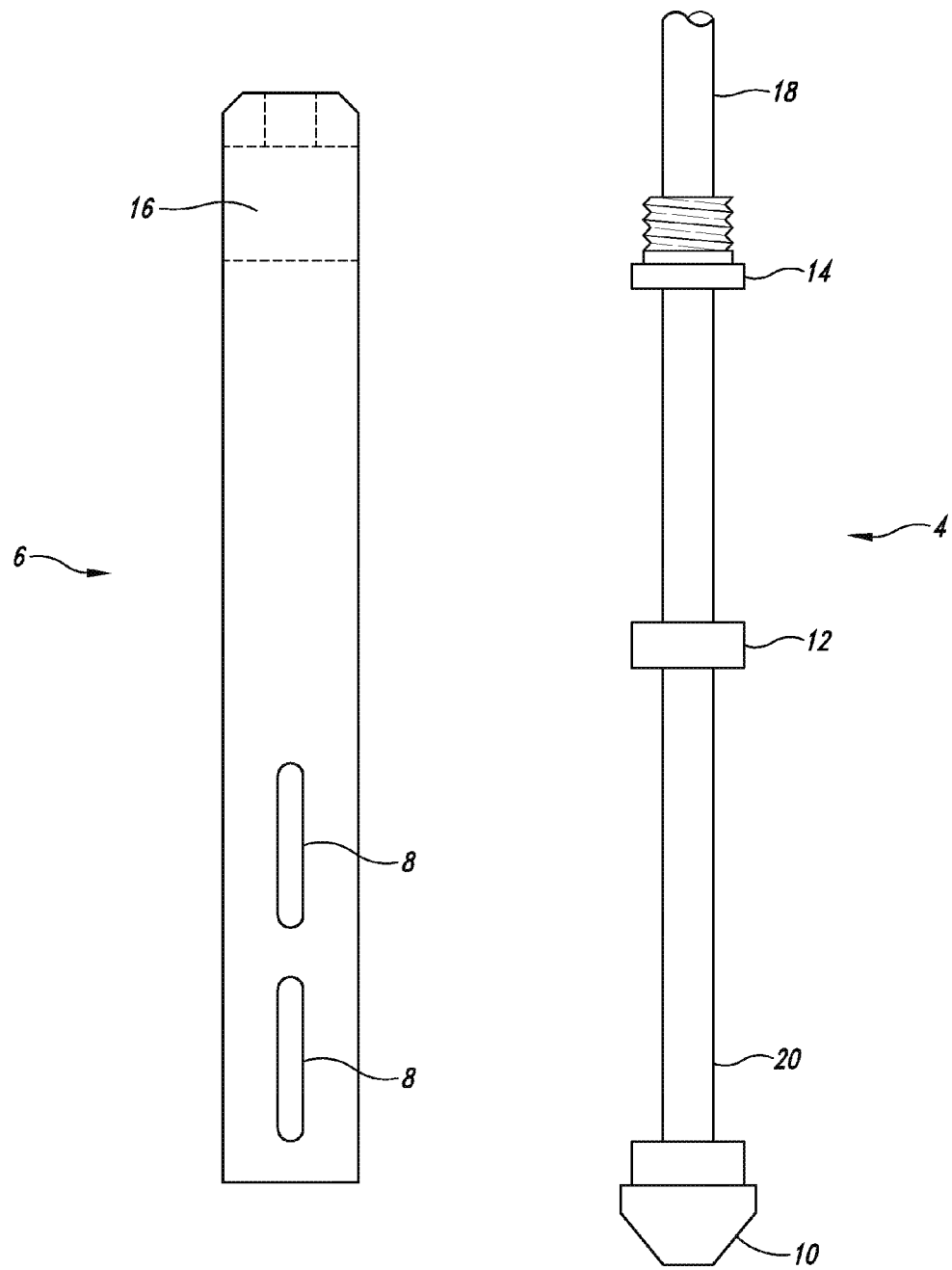

In particular aspects, the present invention provides a surface sampling device for bulk solid foods. The device shaves small pieces of each product that it comes into contact with. The principle operation of the sampling device involves the use of a shaving mechanism to cut slivers from larger pieces of food.

In particular embodiments, and with reference to FIGS. 1A, 1B, 1C and 3, the sampling device 2 comprises a two-part unit having a primary shaft member (e.g., cylindrical stainless steel) 4, and a housing 6 comprising one or more shaving means 8 (in this exemplary embodiment shown as an opening in the housing, the opening framed with a turned-down leading edge and a sharpened trailing edge).

The primary shaft member 4 comprises an end-cap 10, a stationary-piston 12, and a threaded shaft member 14. The end-cap 10 prevents the device from performing a coring action which would limit the amount of discrete samples that may be made. The stationary piston 12 facilitates the removal of shaved/cut food slivers from the shaving tube. The threaded shaft member 14 (counter-clockwise or reverse threaded to ensure that the tube does not unscrew during clockwise or opposite rotary operation) allows the shaving tube to be locked onto the primary shaft during sampling.

The primary shaft 4 acts as the main framework for supporting the shaving tube and (in cooperation with the shaving tube 6) houses collected food shavings, while also acting as a removable stationary piston suitable to expel product collected inside the tube into a sampling bag for further analyses.

The shaving tube 6 comprise a threaded housing member 16, cooperative with the threaded shaft member 14. The shaving tube 6 also comprises one or more openings 8 (e.g., elongated openings running parallel to the tube axis), each opening framed with a turned-down leading edge (refereeing to the direction of rotation) and sharpened trailing-edge to allow the device, during operation, to perform a grating/cutting action. The openings 8 act to slice or shave, and are responsible for contacting food surfaces and shaving slivers of food during rotation of the device. Alternatively, it is possible to use grater type shaving surfaces, or other means suitable to slice or shave pieces from contacted surfaces.

The sampling device 2 is inserted (e.g., into the chuck) in an electric drilling tool to generate the rotary action of the device and allow the slicers (e.g., vertically elongated) to perform cuts of food by passing rapidly over the food surface.

EXAMPLE 1

Novel Sampling Procedure Using the Inventive Sampling Device

In a further aspect, the invention provides a novel sampling procedure, comprising the following steps:

In step 1, placing the shaving tube 6 onto the primary shaft 4.

In step 2, locking the shaving tube 6 into place on the shaft's threaded-housing member 16, using, for example, counter-clockwise threads (reverse threaded with respect to the direction of rotation).

In step 3, the shaft-end of the device 18 is locked into the end of a drill tool.

In step 4, the drill tool is powered on and the sampling device 2 turns, for example, in a clockwise direction at the selected speed allowing the user to take samples from any food surface.

In step 5, the shaving tube 6 is unlocked from the primary shaft 4 (e.g., by turning the tube counter-clockwise).

In step 6, the shaving tube 6 is drawn back passed the stationary piston 12, allowing the sample to be expelled on the exposed portion of the shaft 20.

In step 7, the sample is deposited into a sample collection bag.

EXAMPLE 2

Operating Characteristics Evaluation

As stated herein above, sampling plans for meat products follow two-class attribute plans based on testing for the presence (positive result) or absence (negative result) of an organism. Following conventions set forth by the International Commission on Microbiological Specifications for Foods (ICMSF; 2002. Microorganisms in Foods, Kluwer Academic/Plenum Publishers), for two-class attribute plans the probability of acceptance ($P_a$) for a lot is a function of three factors. The first is the actual incident rate (IR) of *E. coli* O157:H7 in the lot at the sampling point. The second is "n", representing the number of sample units collected for the lot. The third is "c", representing the maximum allowable number of sample units yielding unsatisfactory results for the lot.

Following ICMSF conventions, comparative values of $P_a$ were computed using an operating characteristic function, and depicted as an operating characteristic (OC) curve. OC curves were generated using Sampling Plan Analyzer from Taylor Enterprises, Inc. The function used was to evaluate sampling plans for single defects (positive for pathogen) from a pool of representative stratified samples (where a stratified sample is one where it is specified that equal number of samples should come from different parts of the lots).

Figure 2:
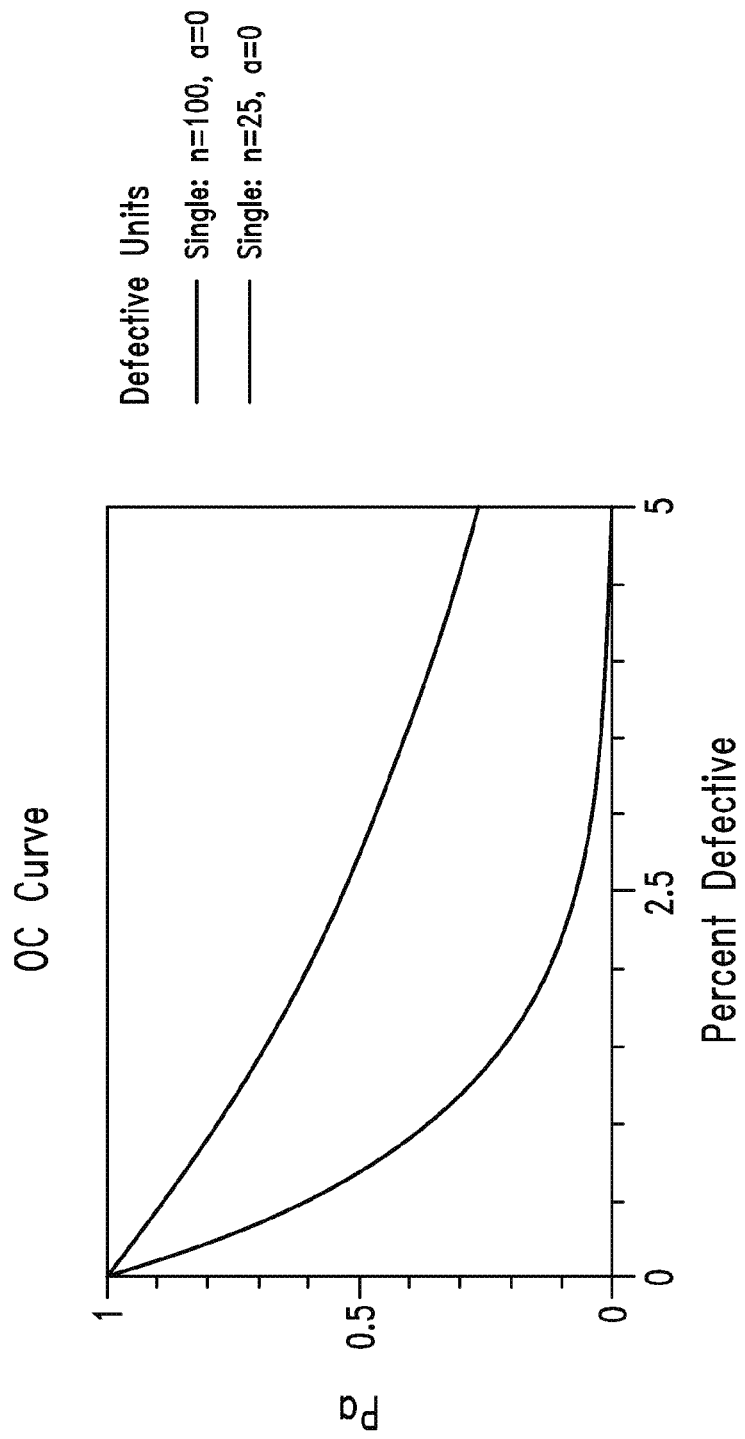
FIG. 2, shows, according to exemplary aspects of the present invention, the difference in power of detection based on sampling an n=25 and n=100.

$P_a$, values were computed by assigning values to each of the three factors described above. First, the incident rates of *E. coli* O157:H7 in fresh beef trim in combo-bins prior to shipping was estimated based on available literature. Second, the "n" values from the two lot acceptance sampling plans were used. Lastly, for the case of zero tolerance, "c" was set to zero (c=0). The difference in power of detection based on sampling an n=25 and n=100 is represented in FIG. 2.

Furthermore, TABLE 1 (below) emphasizes the importance of increasing the number of discrete samples in order to increase power of detection for product contaminated with pathogens. With low sample numbers such as n=5, the probability of accepting a lot that is more contaminated (i.e., 5%) is 77% whereas that using a higher sample number such as n=100 drops to 0.6%. This is a significant difference and illustrates the importance for using a sampling procedure that increases the number of discrete samples taken to ensure that product contaminated with pathogens is not accepted but detected and removed or reworked.

TABLE 1

Probability of acceptance for various incident rates as a function of sampling number (n).

| | Probability of Acceptance ($P_a$) for various n values | | | | | |
|---|---|---|---|---|---|---|
| Incident Rate | $P_a$ for n = 5 | $P_a$ for n = 10 | $P_a$ for n = 15 | $P_a$ for n = 20 | $P_a$ for n = 25 | $P_a$ for n = 100 |
| 0.0 | 1 | 1 | 1 | 1 | 1 | 1 |
| 0.1 | 0.995 | 0.990 | 0.985 | 0.980 | 0.975 | 0.905 |
| 0.2 | 0.990 | 0.980 | 0.970 | 0.961 | 0.951 | 0.819 |
| 0.3 | 0.985 | 0.970 | 0.956 | 0.942 | 0.928 | 0.740 |

TABLE 1-continued

Probability of acceptance for various incident rates as a function of sampling number (n).

Probability of Acceptance ($P_a$) for various n values

| Incident Rate | $P_a$ for n = 5 | $P_a$ for n = 10 | $P_a$ for n = 15 | $P_a$ for n = 20 | $P_a$ for n = 25 | $P_a$ for n = 100 |
|---|---|---|---|---|---|---|
| 0.4 | 0.980 | 0.961 | 0.942 | 0.923 | 0.905 | 0.670 |
| 0.5 | 0.975 | 0.951 | 0.928 | 0.905 | 0.882 | 0.606 |
| 0.6 | 0.970 | 0.942 | 0.914 | 0.887 | 0.860 | 0.548 |
| 0.7 | 0.965 | 0.932 | 0.900 | 0.869 | 0.839 | 0.495 |
| 0.8 | 0.961 | 0.923 | 0.886 | 0.852 | 0.818 | 0.448 |
| 0.9 | 0.956 | 0.914 | 0.873 | 0.835 | 0.798 | 0.405 |
| 1.0 | 0.951 | 0.904 | 0.860 | 0.818 | 0.779 | 0.366 |
| 1.2 | 0.941 | 0.886 | 0.834 | 0.785 | 0.739 | 0.299 |
| 1.4 | 0.932 | 0.868 | 0.809 | 0.754 | 0.703 | 0.244 |
| 1.6 | 0.923 | 0.851 | 0.785 | 0.724 | 0.668 | 0.199 |
| 1.8 | 0.913 | 0.834 | 0.762 | 0.695 | 0.635 | 0.163 |
| 2.0 | 0.904 | 0.817 | 0.739 | 0.668 | 0.603 | 0.133 |
| 2.5 | 0.881 | 0.776 | 0.684 | 0.603 | 0.531 | 0.080 |
| 3.0 | 0.859 | 0.737 | 0.633 | 0.544 | 0.467 | 0.048 |
| 3.5 | 0.837 | 0.700 | 0.586 | 0.490 | 0.410 | 0.028 |
| 4.0 | 0.815 | 0.665 | 0.542 | 0.442 | 0.360 | 0.017 |
| 4.5 | 0.794 | 0.631 | 0.501 | 0.398 | 0.316 | 0.010 |
| 5.0 | 0.774 | 0.599 | 0.463 | 0.358 | 0.277 | 0.006 |

EXAMPLE 3

Additional Embodiment

Figure 4A:
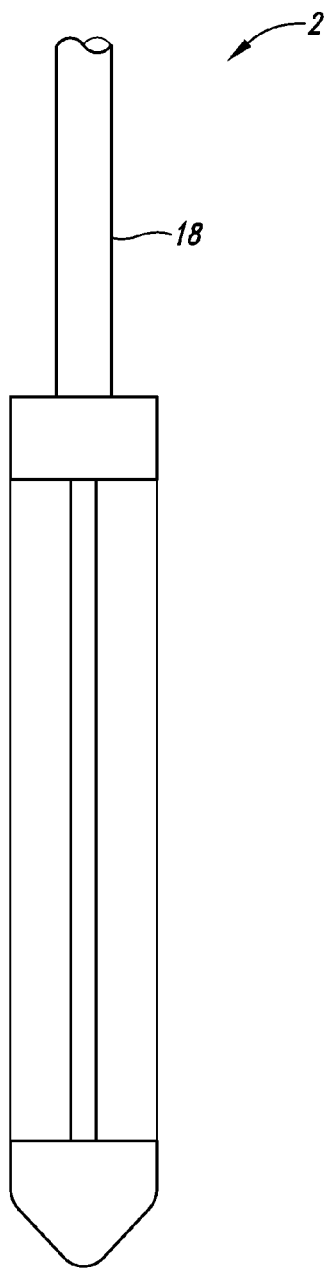
FIG. 4A shows an additional exemplary embodiment of an inventive sampling device.

FIG. 4A shows an additional exemplary embodiment of an inventive sampling device. In this embodiment the sampling device comprises a primary shaft member (e.g., cylindrical stainless steel) terminating in a shaving member (e.g., cylindrical tube). The primary shaft member and the shaving member (e.g., cylindrical shaving tub) may be a single unit formed of a unitary material, may be comprised of two units (e.g., a primary shaft, and a shaving member) permanently jointed (e.g., welded together), or may be removably joined (e.g., by means of threads and thread receiving means). Preferably, the sampling device is a unitary member, or is comprised of a primary shaft member and a shaving member permanently joined (e.g., by welding) to minimize potential contamination areas.

The shaving member (e.g., cylindrical tube) in this example comprises one or more longitudinal (relative to the shaft member) open channels or cavities (e.g., shown as longitudinal fluted openings in the example of FIG. 4A). With respect to a direction of shaving member rotation, each flute is framed with a turned-down leading edge and a sharpened trailing edge such that, during operation, the sampling device performs a grating/cutting action with respect to materials through which it may pass (e.g., food samples, meat samples or trimmings, vegetable samples or trimmings, etc.). During operation (e.g., rotational operation), the fluted openings act to contact the surfaces to be sampled (e.g., food surfaces), and remove (e.g., by excising, slicing, shaving, scraping, etc), samples (e.g., slivers of food). The sampled sample is retained in (e.g., along the bottom) the fluted groove or grooves.

Figure 4B:
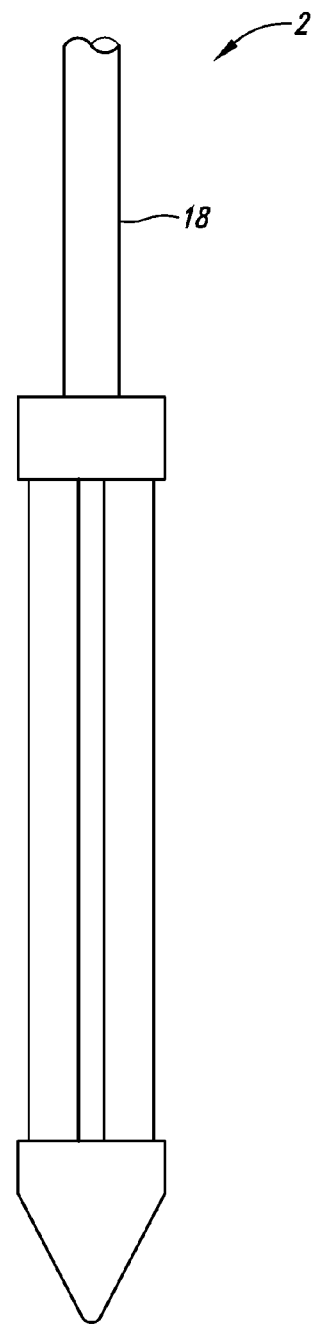
FIG. 4B shows another exemplary embodiment of an inventive sampling device.

FIG. 4B shows another exemplary embodiment. This embodiment is similar to that shown in FIG. 4A. There are three (3) fluted openings, and the cutting edge has an effective higher profile relative to the circumference of the circular shaft, which results in a more aggressive cutting action (e.g., thicker slices are removed from the sample during sampling with the device).

FIGS. 5, 6, 7 and 8 show use of an exemplary embodiment to obtain a sample of a food product (e.g., meat trimmings).

Figure 5:
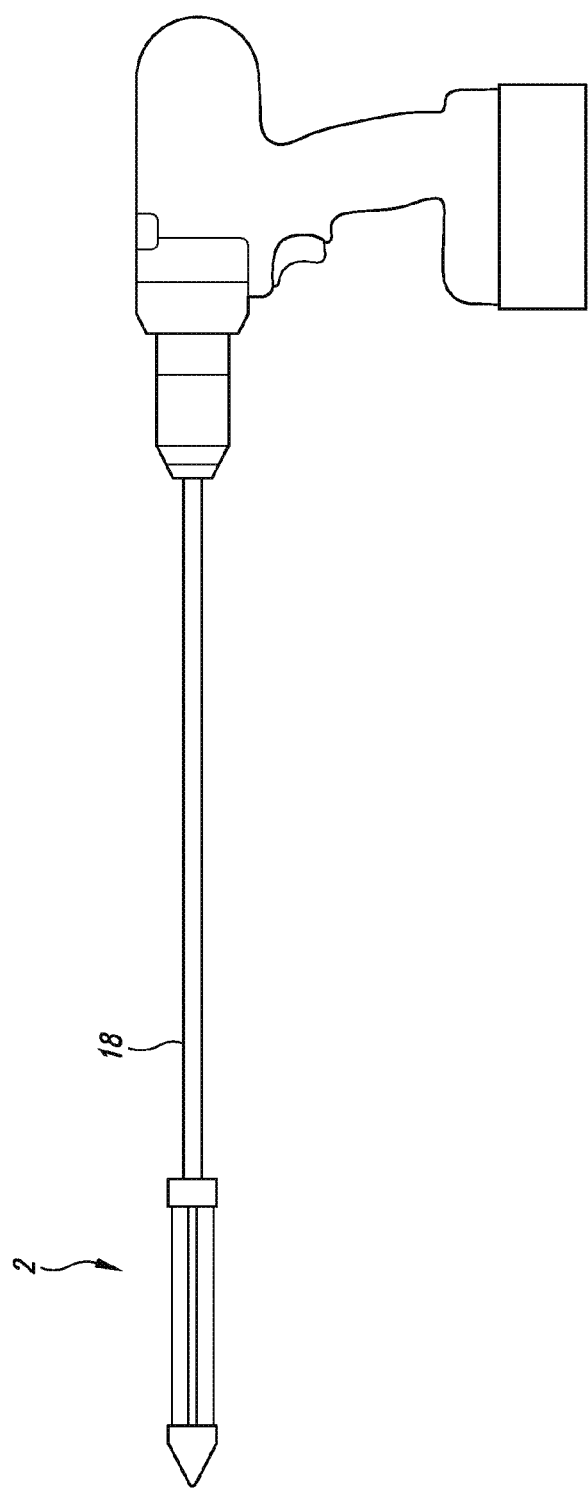
FIGS. 5, 6, 7 and 8 show use of an exemplary embodiment to obtain a sample of a food product (e.g., meat trimmings).

FIG. 5 shows the embodiment of FIG. 4A attached to an electric drill, which provides a preferred means to turn (e.g., rotate) the embodiment as it passes through (e.g., penetrates down through) food being sampled. An electric drill can turn the exemplary sampling device in a reproducible manner, and at a speed sufficient such that the momentum of the cutting edge ensures that a smooth cut ensues instead of 'grabbing' the product.

Alternatively, the exemplary embodiment can be turned by grasping and rotating the shaft by hand. Alternatively, a 't' bar head (e.g., consisting of a short bar affixed at right angles to the main shaft, and at the end opposite of the shaving member (e.g., shaving tube)) can be added or operationally attached to the embodiment, and the embodiment can be turned by grasping the 't' bar head and using it to rotate the shaft.

Figures 1B, 1C:
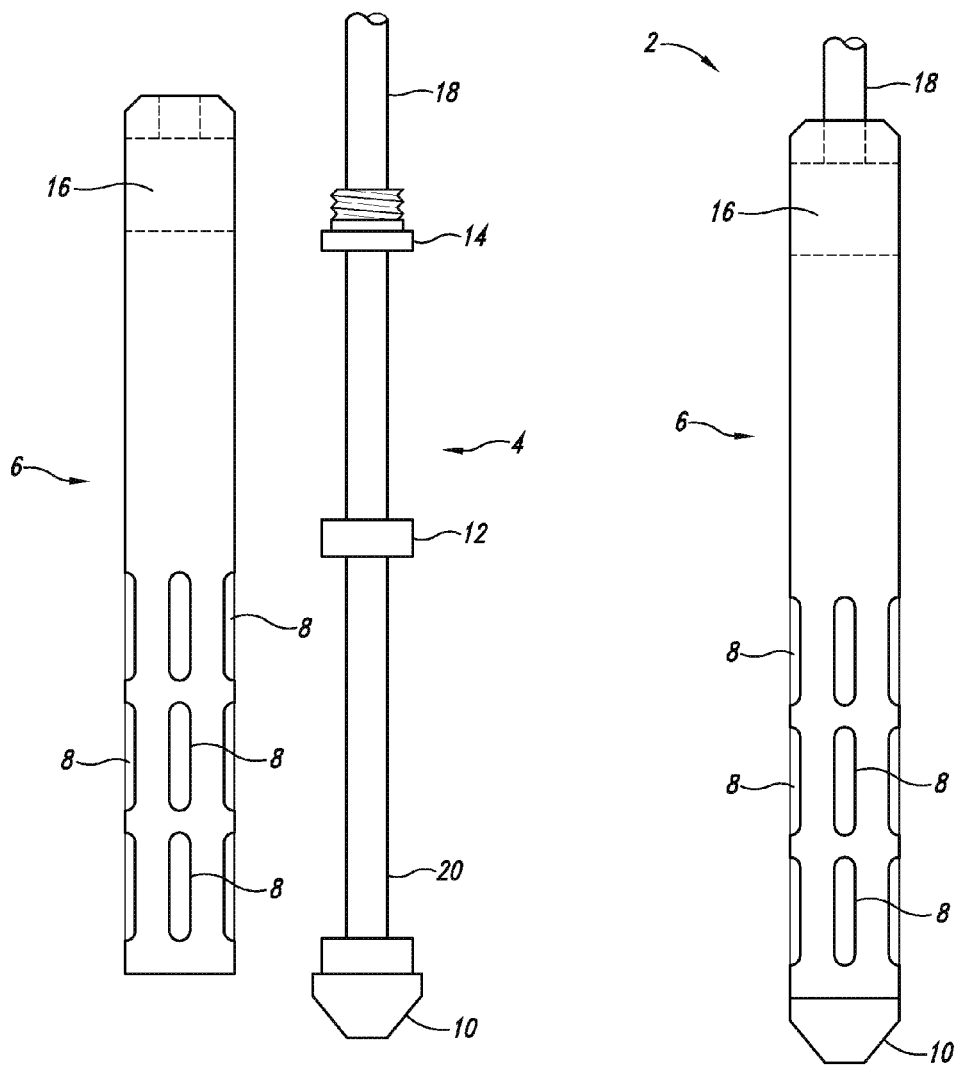
Figure 6:
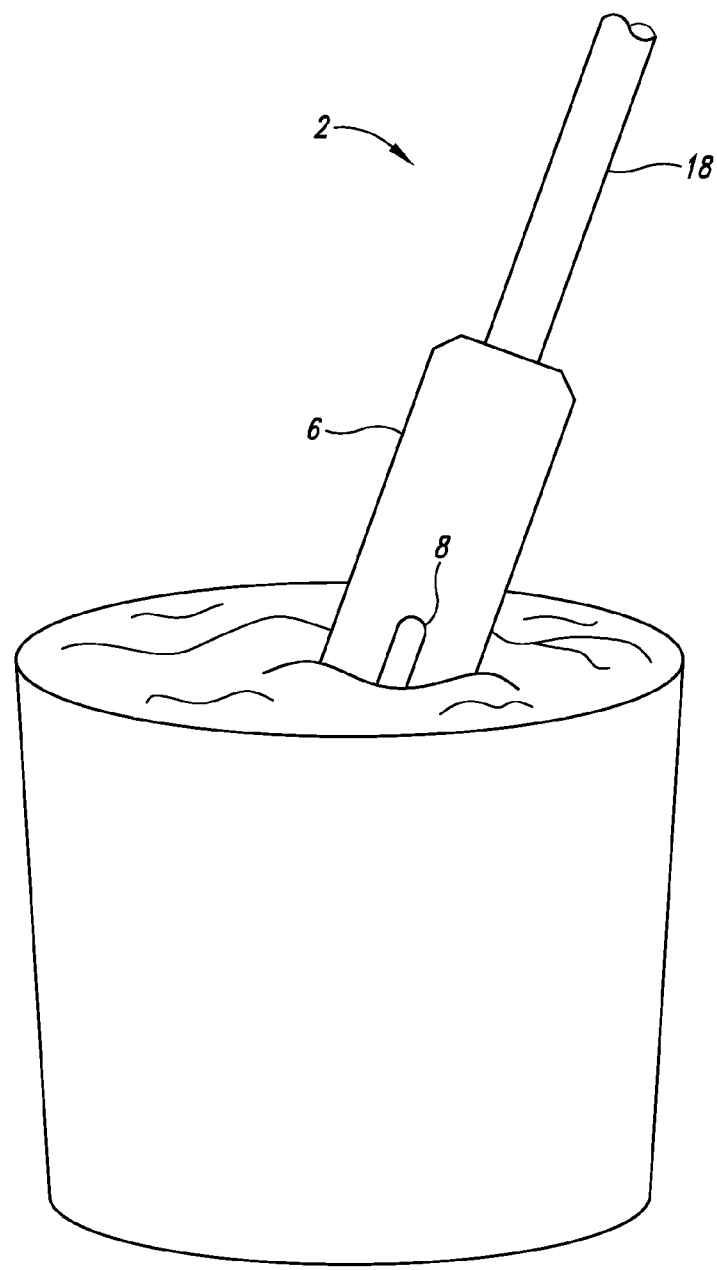

FIG. 6 shows the exemplary embodiment of FIG. 1C used to collect a sample of food. In this example, the food consists of portions of beef approximating the size and nature of those found in 'combos' (combo bins) during the production of beef products.

Figure 7:
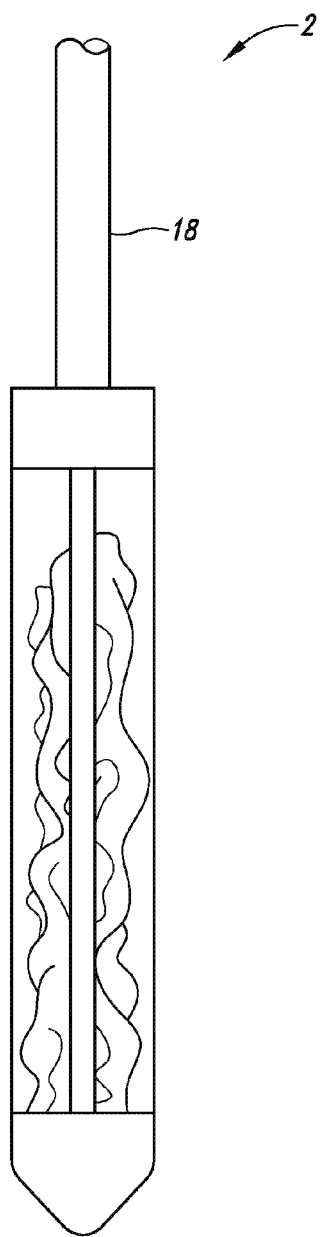

FIG. 7 shows a similar sample collected using the embodiment of FIG. 4A, and shows that the sampled (e.g., shaved and grated) food product is contained in the well of the fluted opening.

Figure 8:
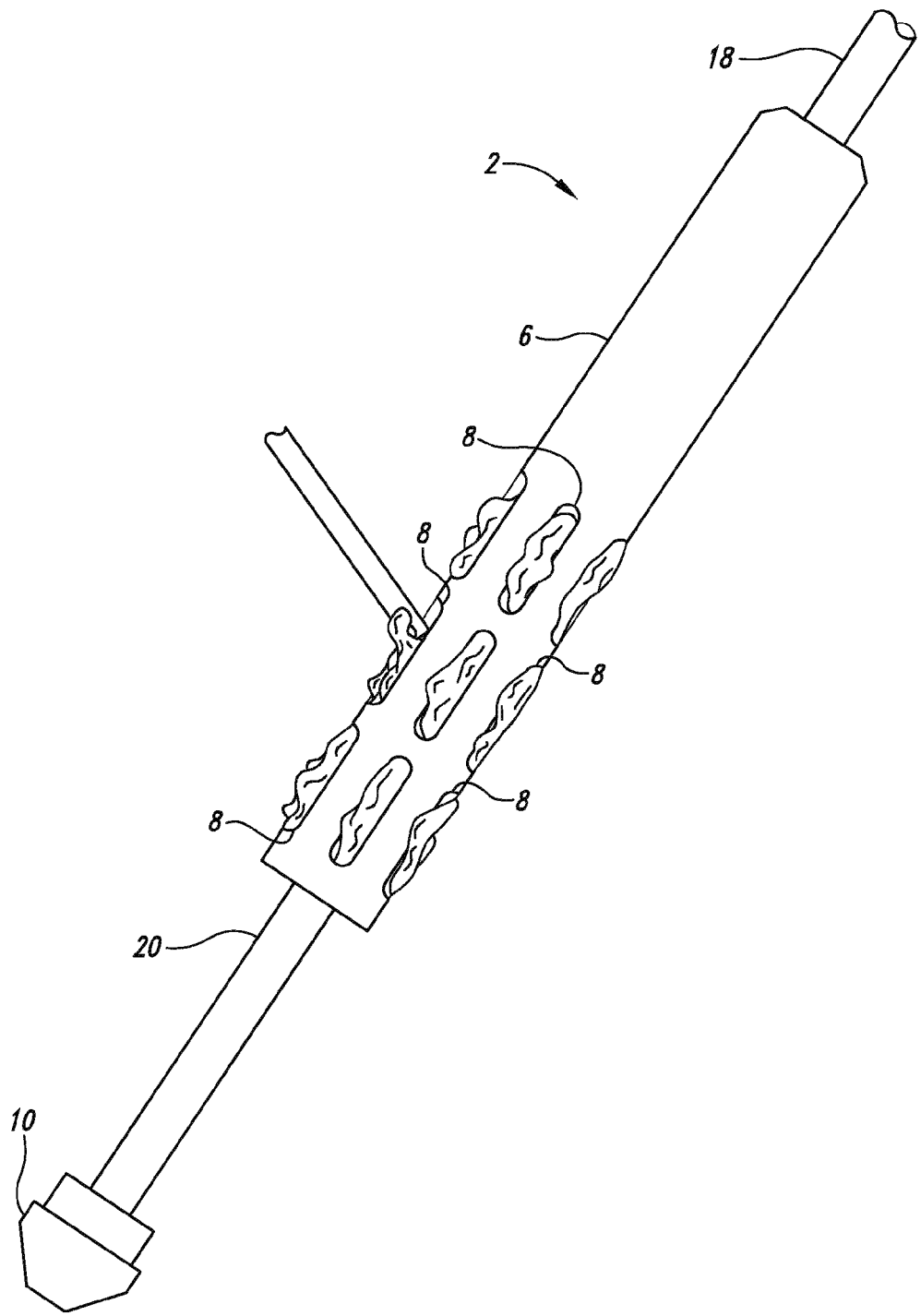

FIG. 8 shows how the sample collected from the embodiment of FIG. 1C can be removed for subsequent laboratory analysis.

Figure 9:
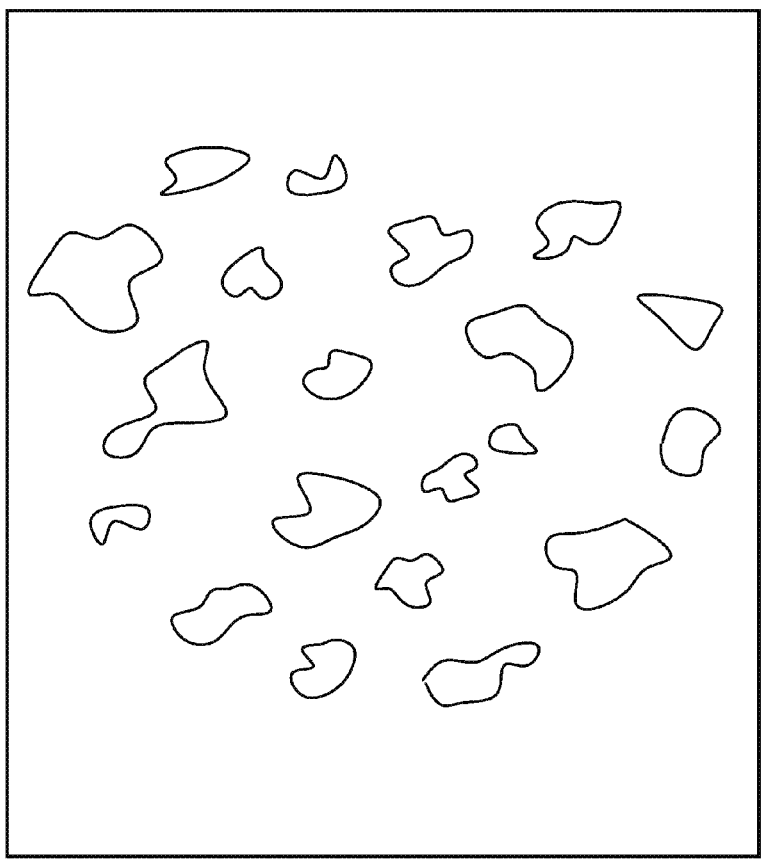
FIG. 9 shows a sample, collected with the embodiment of FIG. 4A, separated into individual pieces.

FIG. 9 shows a sample, collected with the embodiment of FIG. 4A, separated into individual pieces. The number of discrete portions was found to be over 170. In addition, a portion of the sample was found to consist of a 'paste' of discrete portions too small to differentiate. Referring to TABLE 1 of EXAMPLE 2 herein, this number of discrete portions is highly desirable with respect to reducing the probability of accepting a lot containing a low incidence rate of undesirable contaminant.

Figure 10A:
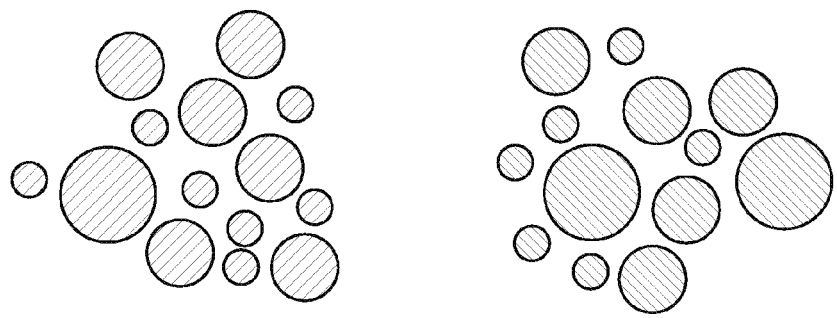
FIGS. 10A, 10B, 10C, 11 and 12 show further aspects of the invention in obtaining a composite sample consisting of a large number of discrete sample units.
Figure 10B:
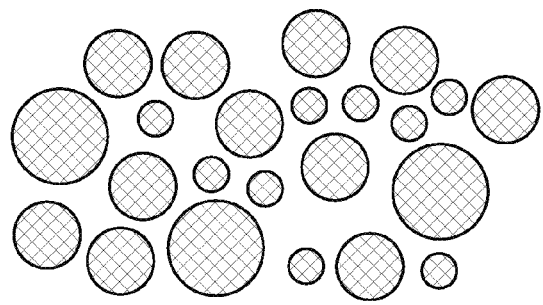
Figure 10C:
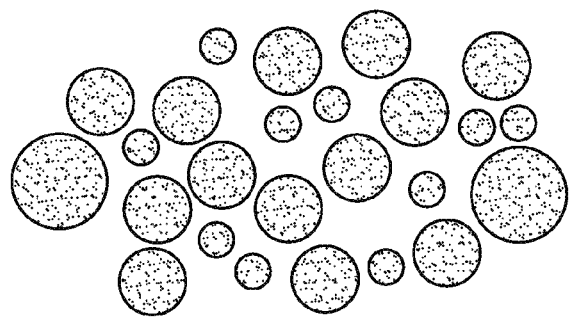

Further investigation of the ability of the invention to obtain a composite sample consisting of a large number of discrete sample units is shown in FIGS. 10A, 10B, 10C, 11 and 12. FIGS. 10A, 10B and 10C show portions of beef (approximating the size and nature of those found in 'combos' during the production of beef products) spray painted to distinctively mark their surfaces. The colored portions of beef were placed into a container similar to that shown in FIG. 6, one color at a time, so as to form a series of discrete colored layers. This collection was sampled using the embodiment of FIG. 4B, and in a manner similar to that shown in FIGS. 5, 6, 7 and 8.

Figure 11:
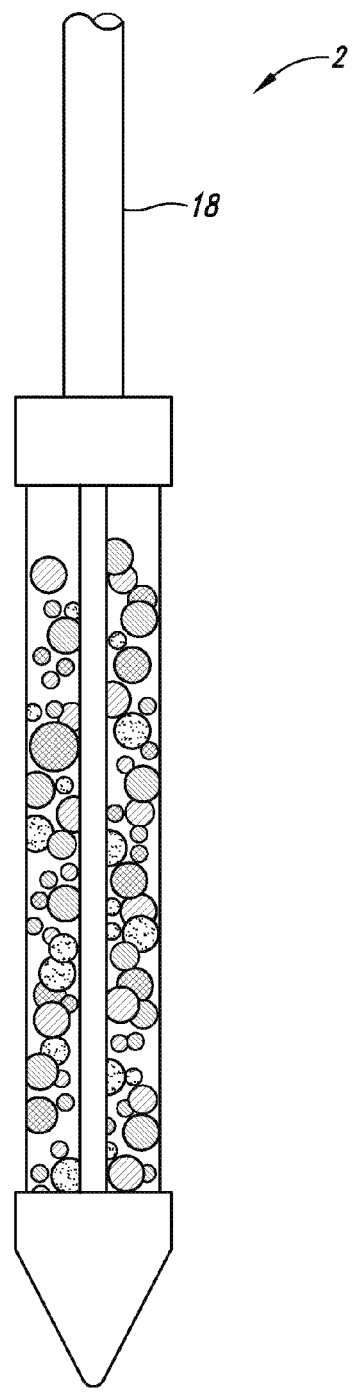
Figure 12:
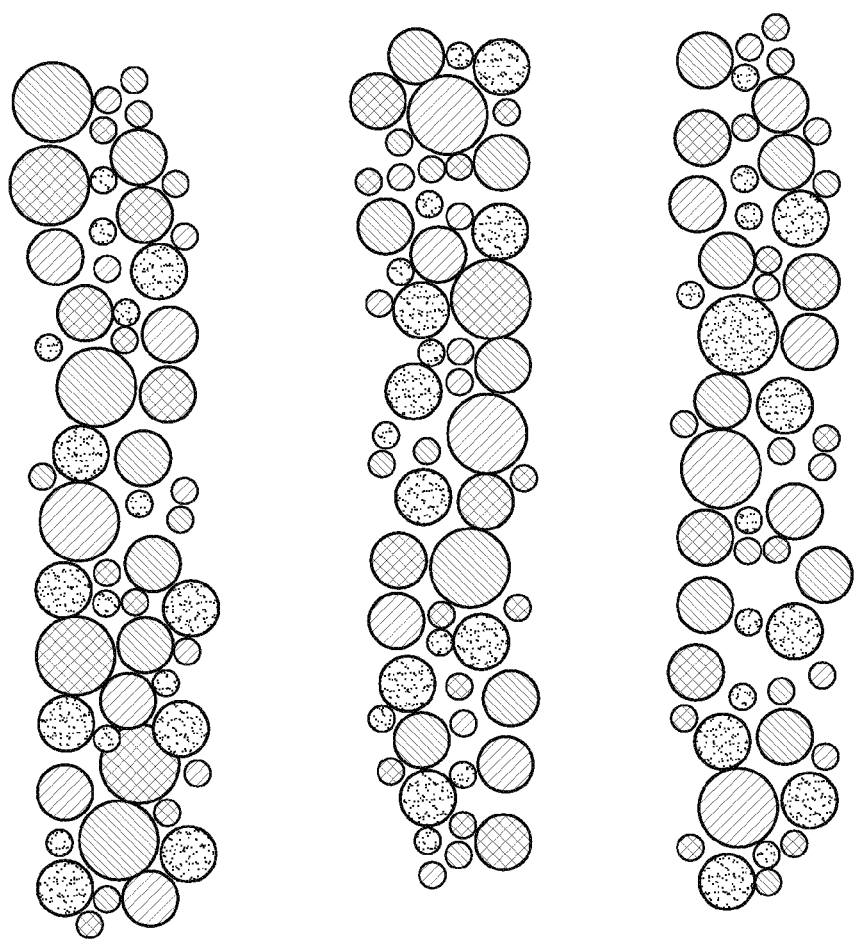

FIG. 11 shows the embodiment of FIG. 4B after it was withdrawn from the container containing the discrete colored layers. As can be seen in FIG. 11, many colors are represented in the collected sample contained in the well of the fluted opening. FIG. 12 shows the collected sample after removal from the well of the fluted opening, and confirms that the embodiment removed discrete portions of material from all of the discrete colored layers present in the container. Again referring to EXAMPLE 2 herein, this result confirms that the embodiment collects a large number of independent sample units from the mass being sampled.

Exemplary Materials of Construction

The device may be constructed of materials which are acceptable in the food industry. Acceptable materials for fabricating the cutting edge include all materials that have previously found use in the food industry. Examples include, but are not limited to the following materials:

Stainless steels—including those metal alloys that consist of about 10.5% or more Chromium (Cr) and more than about 50% Iron (Fe). For example, cutting edges formed from Martensitic, or hardenable stainless steels, are suitable. Martensitic stainless steels by convention are classified in the 400 series, usually with 11.5% chromium up to 18% chromium, with higher levels of carbon than ferritics, and are capable of being heat treated to a wide range of hardness and strength levels. An example of an acceptable Martensitic stainless steel is Grade 420 with alloy composition <0.15% C, 12.0-14.0% Cr, <1.0% Mn, <1.0% Si, <0.04% P, >0.03% S and balance Fe;

Cobalt/Chromium "Superalloy" stainless steels—Examples include the commercial materials Impervium® and Talonite®. The chemical breakdown of Talonite® is <3% Ni, <2% Si, <3% Fe, <3% Mn, 28-32% Cr, <1.5% Mo, 3.5-5.5% Tu, 0.9-1.4% C, and balance Co;

High carbon steels—metal alloys which contain a high proportion of carbon. This type of steel makes the best performing blades in terms of edge retention, toughness and ease of sharpening. It is commonly referred to as tool steel. The drawback associated with high carbon steel is that it is not stain resistant and will rust and discolor over time. An example of an acceptable carbon steel alloy is D-2 is a high carbon tool steel that has a high chromium content (1.5% C, 0.3% Mn, 0.3% Si, 12% Cr, 0.75% Mo and 0.9% V and balance Fe);

Ceramics—Examples include stabilized zirconium oxide commonly used on consumer knives; and Aluminum or aluminum alloys may also be used.

Preferred Design Details

Figure 13:
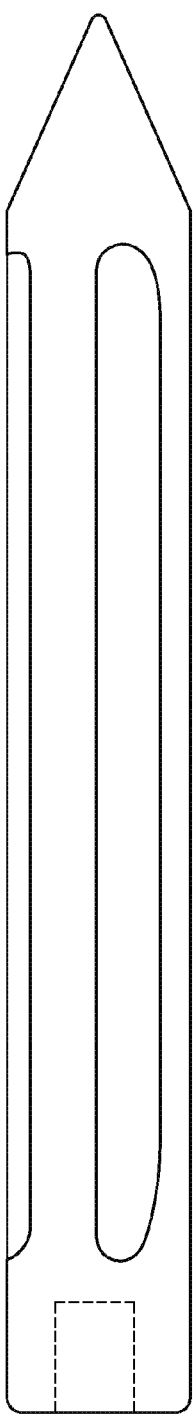
FIG. 13 shows several exemplary devices constructed with vertical (longitudinal) flute openings (e.g., cavities).

Several devices were constructed with vertical (longitudinal) flute openings (e.g., cavities), as shown in FIG. 13. A comparison between a 3-flute design with a beveled cutting edge and a 3-flute design with a non-beveled cutting edge showed that the beveled design with its more aggressive exposed cutting edge collected more distinct pieces of product having a greater size range (from large to small pieces) than the non-beveled version (mostly small pieces). Furthermore the distinct pieces collected by the beveled version composed 37.9% of the total sample weight compared to 30.5% for the non-beveled design, with the remainder in both cases consisting of small shavings and paste too small to differentiate.

Figure 14A:
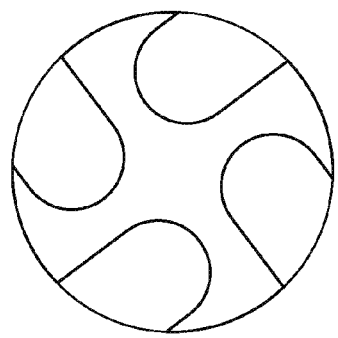
FIGS. 14A, 14B and 14C show several exemplary flute designs.
Figure 14B:
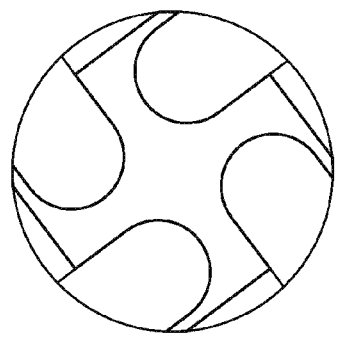
Figure 14C:
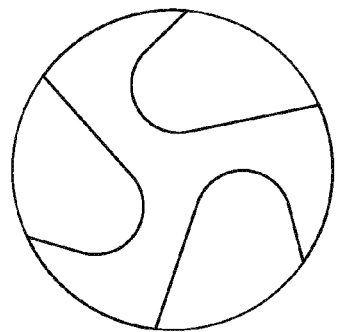

Several exemplary flute designs are shown in FIGS. 14A, 14B and 14C. FIG. 14A shows an exemplary four-flute design with non-beveled cutting edges. FIG. 14B shows an exemplary four-flute design with beveled cutting edges. FIG. 14C shows an exemplary three-flute design with non-beveled cutting edges.

The exemplary devices may comprise one or more sampling openings or channels (e.g., flutes). The only restriction is that the number of flutes times the flute opening size (along the circumference) must be less than the circumference of the shaving tube. The tube itself may be of any diameter. Preferably, the diameter is great enough so that the flute openings can contain enough material to satisfy laboratory sampling requirements. Preferably, the diameter should be small enough so that it is possible to force the shaving tube through the material being sampled without excessive resistance. In the embodiment of FIG. 13, the flute openings of approximately 0.375 inches wide by 1 foot long were machined onto a cutting tube of diameter 1.25 inches. This allowed the collection of between 75 and 100 grams of material, for a test which required 75 grams or more.

An alternative opening/channel/flute arrangement is in the form of a spiral helix. All of the variations in shape, number, and beveled vs. non-beveled cutting edge may still be applied in the context of a helix design The helix angle design will tend to move the collected sample out of the way toward the butt end of the auger, where an optional chamber to store sampled food may be located.

The inventive food sampling devices allow for collection of several hundred discrete samples from food product in less time and with less product loss than current procedures.

The invention claimed is:

1. A surface sampling device for increasing the number of discrete surface samples taken during sampling of a multi-piece sample, comprising:

a cylindrical housing having external and internal surfaces defining a housing wall, a sample-proximal end having an opening therein, a sample-distal end having an opening therein, and an internal channel between the ends, the channel generally defining an axis and a forward direction toward the sample-proximal end;

at least one aperture within the housing wall, the aperture in communication with the internal channel and comprising a directional sample cutting or shaving surface at an external edge thereof, the directional cutting or shaving surface operative with the aperture upon rotation of the housing, to direct cuttings or shavings toward the internal channel; and a shaft member having a diameter less than the internal housing diameter and receivable into the housing at the sample-proximal housing end, the shaft member comprising: a sample-distal shaft end insertable through and extending beyond the sample-distal housing end opening; a sample-proximal shaft end-cap receivable into the sample-proximal housing end opening to seal the opening; a shaft attachment member positioned on the shaft between the distal shaft end and the shaft end-cap, the attachment member receivable into the sample-distal housing end and positioned at a distance from the shaft end-cap to hold the end-cap in sealable communication with the sample-proximal housing end opening; and a piston in communication with the internal housing surface and positioned on the shaft between the shaft attachment member and the shaft end-cap and defining a sample collecting chamber within the internal channel between the piston and the end-cap, and wherein the at least one aperture is in communication with the collecting chamber.

2. The surface sampling device of claim 1, wherein the shaft attachment member is threaded and receivable into complementary thread receiving means in the sample-distal housing end to lock the housing onto the shaft.

3. The surface sampling device of claim 1, wherein the threads are reverse threaded with respect to an operative rotational direction of the sampling device.

4. The surface sampling device of claim 1, wherein the at least one aperture comprises an elongated opening running parallel to the housing channel axis.

5. The surface sampling device of claim 1, wherein the at least one aperture is framed with a turned-down or beveled leading edge, with respect to a direction of rotation, and a sharpened trailing edge to allow the device, during rotational operation thereof to perform a cutting or shaving action.

6. The surface sampling device of claim 1, comprising a plurality of apertures positioned randomly along the wall of the sample collecting chamber.

7. The surface sampling device of claim 1, comprising a plurality of apertures positioned in a symmetrical array along the wall of the sample collecting chamber.

8. The surface sampling device of claim 1, wherein the shaft diameter is less than one-half the outside diameter of the piston.

9. A method for enhanced sampling of multi-piece samples, comprising:
   obtaining a test sample comprising multiple pieces;
   rotating the sampling device of claim 1 by rotating the sample-distal shaft end extending beyond the sample-distal housing end opening;
   introducing the rotating sampling device into the test sample to obtain multiple sample surface cuttings or shavings from the multiple pieces or from a representative fraction thereof; and
   recovering the multiple sample surface cuttings or shavings from the device to provide for a collected sample comprising discrete surface samples.

10. The method of claim 9, wherein introducing comprises at least one repetition of forward introduction of the device into the test sample and retrieval of the device in the reverse direction from the test sample.

11. The method of claim 10, comprising a plurality of repetitions through different sampling paths within the test sample.

12. The method of claim 9, wherein recovering the multiple sample surface cuttings or shavings from the device comprises: unlocking the shaft from the housing; removing the shaft from the housing to expose the piston; and recovering the surface cuttings or shavings from the sample collecting chamber and the at least one aperture.

13. A surface sampling device for increasing the number of discrete surface samples taken during sampling of a multi-piece sample, comprising:
   a cylindrical member having an external surface, a sample-proximal end, a sample-distal end, the cylindrical member generally defining an axis and a forward direction toward the sample-proximal end;
   at least one channel closed at both ends in the axial direction within the external surface of the cylindrical member, and having a leading-edge and a trailing-edge each at or inward of the cylindrical surface adjacent the channel, the channel extending into the cylindrical member from the external surface thereof, the channel comprising an open sample collection chamber and a directional sample cutting or shaving surface at an external trailing-edge thereof, the directional cutting or shaving surface operative with the channel, upon rotation of the cylindrical member, to direct cuttings or shavings into the channel and collection chamber; and
   a cylindrical shaft integral with, or lockingly receivable into the cylindrical member at the sample distal end thereof, the cylindrical shaft suitable to operatively rotate the cylindrical member when rotational force is applied to the cylindrical shaft.

14. The surface sampling device of claim 13, wherein the at least one channel comprises an elongated opening running parallel to the axis of the cylindrical member.

15. The surface sampling device of claim 13, wherein the at least one channel is framed with a turned-down or beveled leading edge, with respect to a direction of rotation, and a sharpened trailing edge to allow the device, during rotational operation thereof to perform a cutting or shaving action.

16. The surface sampling device of claim 13, comprising a plurality of channels positioned randomly along the external surface of the cylindrical member.

17. The surface sampling device of claim 13, comprising a plurality of channels positioned in a symmetrical array along the external surface of the cylindrical member.

* * * * *